(12) United States Patent
Cohen et al.

(10) Patent No.: US 7,792,563 B2
(45) Date of Patent: Sep. 7, 2010

(54) METHOD AND APPARATUS FOR THE GUIDED ABLATIVE THERAPY OF FAST VENTRICULAR ARRHYTHMIA

(75) Inventors: Richard J. Cohen, Chestnut Hill, MA (US); Maya Barley, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1088 days.

(21) Appl. No.: 11/376,994

(22) Filed: Mar. 16, 2006

(65) Prior Publication Data

US 2007/0219452 A1  Sep. 20, 2007

(51) Int. Cl.
    *A61B 5/04* (2006.01)
(52) U.S. Cl. .................. 600/373; 600/515; 606/45; 606/46
(58) Field of Classification Search .......... 606/32–34, 606/507–508; 600/515–516, 373, 509, 518, 600/544, 101
See application file for complete search history.

(56) References Cited

U.S. PATENT DOCUMENTS

| | | | |
|---|---|---|---|
| 5,172,690 A * | 12/1992 | Nappholz et al. ............ 607/13 |
| 5,311,873 A | 5/1994 | Savard et al. |
| 6,308,094 B1 | 10/2001 | Shusterman et al. |
| 6,370,412 B1 | 4/2002 | Armoundas et al. |
| 2002/0123747 A1 * | 9/2002 | Wentzel et al. ............. 606/41 |
| 2004/0059237 A1 * | 3/2004 | Narayan et al. ............ 600/509 |
| 2006/0270915 A1 * | 11/2006 | Ritter et al. ............... 600/300 |
| 2007/0060829 A1 * | 3/2007 | Pappone ................... 600/509 |

OTHER PUBLICATIONS

International Search Report of the International Searching Authority for International Application No. PCT/US07/06620 mailed Feb. 20, 2008.
Written Opinion of the International Searching Authority for International Application No. PCT/US07/06620 mailed Feb. 20, 2008.

* cited by examiner

*Primary Examiner*—Linda C Dvorak
*Assistant Examiner*—Jaymi Della

(57) ABSTRACT

Method and apparatus for guiding ablative therapy of abnormal biological electrical excitation. The excitation from the previous excitatory wave is significant at the beginning of the next excitation. In particular, it is designed for treatment of fast cardiac arrhythmias. Electrical signals are acquired from recording electrodes, and an inverse dipole method is used to identify the site of origin of an arrhythmia. The location of the tip of an ablation catheter is similarly localized from signals acquired from the recording electrodes while electrical pacing energy is delivered to the tip of the catheter close to or in contact with the cardiac tissue. The catheter tip is then guided to the site of origin of the arrhythmia, and ablative radio frequency energy is delivered to its tip to ablate the site.

16 Claims, 2 Drawing Sheets

METHOD AND APPARATUS FOR THE GUIDED ABLATIVE THERAPY OF FAST VENTRICULAR ARRHYTHMIA

GOVERNMENT SUPPORT

This invention was made with government support under Grant Number NCC958-3, awarded by NASA. The government has certain rights in the invention.

BACKGROUND OF THE INVENTION

This invention relates to method and apparatus for guided ablative therapy and more particularly to such therapy to treat fast ventricular arrhythmia.

The electrical activity generated in certain organs in the human body is intimately related to the organs' functions. Abnormalities in cardiac and brain electrical conduction processes are principal causes of morbidity and mortality in the developed world. Appropriate treatment of disorders arising from such abnormalities frequently requires a determination of their location. Such localization of the site of origin of an abnormal electrical excitation is typically achieved by painstaking mapping of the electrical activity on the inner surface of the heart or the brain from electrodes or a catheter. Often, this recording must be done while the abnormal biological electrical excitation is ongoing.

Radio frequency catheter ablation procedures have evolved in recent years to become an established treatment for patients with a variety of supraventricular [Lee, 1991; Langberg, 1993] and ventricular arrhythmias [Stevenson, 1997; Stevenson, 1998]. However, in contrast to supraventricular tachycardia ablation, which is highly successful because the atrio-ventricular node anatomy is known, ventricular tachycardia ablation remains difficult because the site of origin of the arrhythmia could be anywhere in the ventricles.

Sustained ventricular tachycardia is often a difficult arrhythmia to manage. One of the most common indications for radio frequency catheter ablation of ventricular tachycardia is arrhythmia refractory to drug therapy that results in frequent discharges from an implantable cardioverter-defibrillator. Radio frequency ablation is also indicated when the ventricular tachycardia is too slow to be detected by the implantable cardioverter-defibrillator or is incessant [Strickberger, 1997].

Selection of the appropriate target sites for ablation is usually based on a combination of anatomical and electrical criteria. The ability of the physician to deliver radio-frequency energy through a catheter at the reentry site is restricted by the limitations of the current technology that is employed to guide the catheter to the appropriate ablation site. The principal limitation of the radio frequency ablation technique is the determination of the correct site for delivery of the radio frequency energy. Conventionally, this determination is achieved by painstaking mapping of the electrical activity on the inner surface of the heart from electrodes on the catheter. Often, this recording must be done while the arrhythmia is ongoing. This is a major problem, especially for those arrhythmias which compromise hemodynamic function of the patient. Many arrhythmias for this reason are not presently amenable to radio frequency ablation treatment.

The acute lesion created by radio frequency current consists of a central zone of coagulation necrosis surrounded by a zone of hemorrhage and inflammation. Arrhythmias may recur if the target tissue is in the border zone of a lesion instead of in the central area of necrosis. If the inflammation resolves without residual necrosis, arrhythmias may recur several days to several weeks after an apparently successful ablation [Langberg, 1992]. Conversely, an arrhythmia site of origin that was not initially successfully ablated may later become permanently nonfunctional if it lies within the border zone of a lesion and if microvascular injury and inflammation within this zone result in progressive necrosis [Nath, 1994]. Thus, the efficacy and long term outcome of catheter ablation depend on accurate determination of the site of origin of the arrhythmia.

Catheter ablation of sustained monomorphic ventricular tachycardia late after myocardial infarction has been challenging. These arrhythmias arise from reentry circuits that can be large and complex, with broad paths and narrow isthmuses, and that may traverse subendocardial, intramural, and epicardial regions of the myocardium [deBakker, 1991; Kaltenbrunner, 1991]. Mapping and ablation are further complicated by the frequent presence of multiple reentry circuits, giving rise to several morphologically different ventricular tachycardias [Wilbur, 1987; Waspel, 1985]. In some cases, different reentry circuits form in the same abnormal region. In other cases, reentry circuits form at disparate sites in the infarct area. The presence of multiple morphologies of inducible or spontaneous ventricular tachycardia has been associated with antiarrhythmic drug inefficacy [Mitrani, 1993] and failure of surgical ablation [Miller, 1984].

Several investigators have reported series of studies of patients selected for having one predominant morphology of ventricular tachycardia ("clinical ventricular tachycardia") who were treated with radio frequency catheter ablation [Morady, 1993; Kim, 1994]. It is likely that this group of patients represents less than 10% of the total population of patients with ventricular tachycardia [Kim, 1994]. The patient must remain hemodynamically stable while the arrhythmia is induced and maintained during mapping. The mapping procedure may take many hours during which the arrhythmia must be maintained. Thus, currently, radio frequency catheter ablation is generally limited to "slow" ventricular tachycardia (about 130 bpm) which is most likely to be hemodynamically stable.

Ablation directed towards the "clinical tachycardia" that did not target other inducible ventricular tachycardias successfully abolished the "clinical ventricular tachycardia" in 71% to 76% cases. However, during follow-up up to 31% of those patients with successful ablation of the "clinical ventricular tachycardia" had arrhythmic recurrences, some of which were due to different ventricular tachycardia morphologies from that initially targeted for ablation.

Furthermore, there are several difficulties in selecting a dominant, "clinical ventricular tachycardia" for ablation. Often it is not possible to determine which ventricular tachycardia is in fact the one that has occurred spontaneously. In most cases, only a limited recording of one or a few ECG leads may be available. In patients with implantable defibrillators ventricular tachycardia is typically terminated by the device before an ECG is obtained. Even if one ventricular tachycardia is identified as predominant, other ventricular tachycardias that are inducible may subsequently occur spontaneously. An alternative approach is not to consider the number of ventricular tachycardia morphologies in determining eligibility for catheter ablation but rather to attempt ablation of all inducible ventricular tachycardias that are sufficiently tolerated to allow mapping [Stevenson, 1998b; Stevenson, 1997]. However, this approach requires that the patient be hemodynamically stable during the ventricular tachycardia mapping procedure.

The use of fluoroscopy (digital bi-plane x-ray) for the guidance of the ablation catheter for the delivery of the curative radio frequency energy is common to clinical catheter ablation strategies. However, the use of fluoroscopy for these purposes may be problematic for the following reasons: (1) It may not be possible to accurately associate intracardiac electrograms with their precise location within the heart; (2) The endocardial surface is not visible using fluoroscopy, and the target sites can only be approximated by their relationship with nearby structures such as ribs and blood vessels as well as the position of other catheters; (3) Due to the limitations of two-dimensional fluoroscopy, navigation is frequently inexact, time consuming, and requires multiple views to estimate the three-dimensional location of the catheter; (4) It may not be possible to accurately return the catheter precisely to a previously mapped site; (5) It is desirable to minimize exposure of the patient and medical personnel to radiation; and (6) Most importantly, fluoroscopy cannot identify the site of origin of an arrhythmia and thus cannot be used to specifically direct a catheter to that site.

Electro-anatomic mapping systems (e.g., Carto, Biosense, Marlton, N.J.) provide an electro-anatomical map of the heart. This method of nonfluoroscopic catheter mapping is based on an activation sequence to track and localize the tip of the mapping catheter by magnetic localization in conjunction with electrical activity recorded by the catheter. This approach has been used in ventricular tachycardia [Nademanee, 1998; Stevenson, 1998], atrial flutter [Shah, 1997; Nakagawa, 1998], and atrial tachycardia ablation [Natale, 1998; Kottkamp, 1997]. The ability to localize in space the tip of the catheter while simultaneously measuring the electrical activity may facilitate the mapping process. However, this technique fundamentally has the limitation that it involves sequentially sampling endocardial sites. The mapping process is prolonged while the patients must be maintained in ventricular tachycardia. Also, the localization is limited to the endocardial surface and thus sites of origin within the myocardium cannot be accurately localized.

The basket catheter technique employs a non-contact 64-electrode basket catheter (Endocardial Solutions Inc., St. Paul, Minn.) placed inside the heart to electrically map the heart. In the first part of this procedure high frequency current pulses are applied to a standard catheter used in an ablation procedure. The tip of this catheter is dragged over the endocardial surface, and a basket catheter is used to locate the tip of the ablation catheter and thus to trace and reconstruct the endocardial surface of the ventricular chamber. Then the chamber geometry, the known locations of the basket catheter, and the non-contact potential at each electrode on the basket catheter are combined in solving Laplace's equation, and electrograms on the endocardial surface are computed. This technique has been used in mapping atrial and ventricular arrhythmias [Schilling, 1998; Gomick, 1999]. One of the drawbacks of this methodology is that the ventricular geometry is not fixed but varies during the cardiac cycle. In addition, the relative movement between the constantly contracting heart and the electrodes affects the mapping. While the inter-electrode distances on each sidearm of the basket catheter are fixed, the distances between the actual recording sites on the endocardium decrease during systole. This leads to relative movement between the recording electrode and the tissue, significantly limiting the accuracy of the mapping method. Also, the localization is limited to the endocardial surface, and thus sites of origin within the myocardium cannot be accurately localized.

U.S. Pat. Nos. 6,308,093 and 6,370,412, the contents of which are incorporated herein by reference, present a method in which a single equivalent moving dipole (SEMD) model can be used to localize an electrical source within the body. One of the co-inventors of the present application is a co-inventor of these two patents. The concept of considering the heart as a single dipole generator originated with Einthoven [Einthoven, 1912], and its mathematical basis was established by Gabor and Nelson [Gabor, 1954]. Several investigators [Mirvis, 1981; Gulrajani, 1984], [Tsunakawa, 1987] have studied the cardiac dipole in clinical practice and attempted to determine the dipolar nature of the ECG. The advantages of the use of the equivalent cardiac dipole are: (1) It permits quantification of source strength in biophysical terms that are independent of volume conductor size (classic electrocardiography), and (2) The active equivalent source can be localized and assigned a location, something that cannot be done using classical electrocardiography.

For many arrhythmias, the electrical activity within the heart is highly localized for a portion of the cardiac cycle. During the remainder of the cardiac cycle the electrical activity may become more diffuse as the waves of electrical activity spread. It is not possible to construct the three-dimensional distribution of cardiac electrical sources from a two-dimensional distribution of ECG signals obtained on the body surface. However, if it is known that a source is localized, then this localized source can be approximated as a single equivalent moving dipole (SEMD), for which one can compute the dipole parameters (i.e., location and moments) by processing electrocardiographic signals acquired from recording electrodes placed on the body surface or in the body.

As described in U.S. Pat. Nos. 6,308,093 and 6,370,412, fitting the dipole parameters to body surface ECG signals provides a solution for the dipole location as well as for its strength and orientation (referred to herein as the "Inverse Dipole Method"). The location of the dipole at the time epoch when the electrical activity is confined to the vicinity of the site of origin of an arrhythmia should coincide with the site of origin of the arrhythmia. In contrast to standard mapping techniques, the inverse solution can be computed from only a few beats of the arrhythmia, thereby eliminating the need for prolonged maintenance of the arrhythmia during the localization process.

In previous methods [Armoundas, 1999; Armoundas, 2001; Armoundas, 2003] after the site of origin of the arrhythmia is localized, one or more electrodes at the ablation catheter tip are used to deliver low-amplitude (sub-threshold) bipolar current pulses, and the resulting signals are recorded and processed to locate the position of the catheter tip dipole using the same Inverse Dipole Method. The catheter tip is guided towards the site of origin of the arrhythmia using the relative calculated locations of the respective dipoles. When the catheter tip dipole and arrhythmic site dipole are calculated to have nearly identical locations, the location of the actual catheter tip should also nearly coincide with the site of origin of the arrhythmia. Ablative energy is then delivered. This method of source localization and catheter guidance shall be referred to herein as the "Inverse Dipole Method".

When the rate of the ventricular tachycardia is low, the electrical activity from the previous cardiac cycle is no longer present when the next cardiac cycle begins. On the other hand, if the ventricular tachycardia is fast, electrical activity from the previous cycle, now for the most part remote from the site of origin of the arrhythmia, is still present when the next wave of depolarization emerges from that site. The bioelectric source dipole is computed from the body surface potentials which in turn reflect a summation of all on-going electrical activity in the heart. At the start of the QRS complex during fast ventricular tachycardia the bioelectrical source dipole will be a summation of both the remote electrical activity associated with the previous cardiac cycle and the localized activity newly emerging from the site of origin of the arrhythmia. Consequently, the location of the bioelectric source dipole will no longer correspond to the location of the site of origin of the arrhythmia. Therefore, even if the catheter tip and site of origin of the arrhythmia are in reality superposed, the previously described method will identify their locations as being different. It is clear that the method described previously for localizing the arrhythmic site dipole will work only in the context of slow ventricular tachycardia.

What is needed is a means of efficiently directing the tip of a catheter to the site of origin of both slow and fast arrhythmias to allow the Inverse Dipole Method to be used in all contexts.

SUMMARY OF THE INVENTION

According to a first aspect, the method of the invention for locating the site of origin of an arrhythmia includes applying a multiplicity of recording electrodes to the body. Electrical activity from the recording electrodes is analyzed to identify the location of the site of origin of the arrhythmia. One or more stimulating electrodes is introduced into the body and the heart is stimulated with supra-threshold stimuli through the one or more stimulating electrodes. The electrical activity from the recording electrodes is processed to identify the locations of the one or more stimulating electrodes in relation to the location of the site of origin of the arrhythmia. In a preferred embodiment, radio frequency energy is delivered to the location of the site of origin of the arrhythmia to ablate the site. The arrhythmia may be initiated by electrical stimulation of the heart. The analyzing step may be preformed at a multiplicity of time epochs during the cardiac cycle and may involve computing the location of at least one equivalent moving dipole.

The analyzing step, in one embodiment, involves the application of a set of criteria to the analysis of electrical activity at the multiplicity of time epochs in order to determine the site of origin of the arrhythmia. The criteria may measure the degree of correlation of direction of movement between successive dipoles, and/or the magnitude of the dipole and/or the dipole moment and/or the degree of fit of the dipole model to the measured data and/or other dipole parameters. The location of the site of origin of the arrhythmia may be displayed on a display serving as a graphical user interface.

In another aspect, the invention is a system for locating the site of origin of an arrhythmia including a multiplicity of recording electrodes adapted for attachment to a body. Signal processing equipment analyses the electrical activity from the recording electrodes to identify the location of the site of origin of the arrhythmia. Stimulating electrodes are provided for introduction into the body for stimulating the heart with supra-threshold stimuli. A computer system processes the electrical activity from the recording electrodes to identify the locations of the one or more stimulating electrodes in relation to the location of the site of origin of the arrhythmia. In a preferred embodiment of this aspect of the invention the system includes circuitry for delivering radio frequency energy to ablate the site of origin of the arrhythmia.

In preferred embodiments the methods of the present invention involve applying a multiplicity of recording electrodes to the body, analyzing the electrical activity from the recording electrodes to identify the location of the site of origin of the arrhythmia, introducing one or more stimulating electrodes into the body, stimulating the heart with supra-threshold stimuli through the one or more stimulating electrodes, and processing the electrical activity from the recording electrodes to identify the locations of the one or more stimulating electrodes—this latter electrical activity reflects the signals emanating from both the stimulating electrode(s) and from the heart due to the stimuli from the stimulating electrode(s).

In a preferred embodiment, the arrhythmia is initiated by means of electrical stimulation of the heart. The analyzing step is used to identify the location of the site of origin of the arrhythmia by analyzing the electrical activity at a multiplicity of time epochs during the cardiac cycle. In a particularly preferred embodiment, the analyzing step involves computing the location of at least one equivalent moving dipole from the acquired signals. A set of criteria may be applied to the analyses of electrical activity at a multiplicity of time epochs in order to determine the site of origin of the arrhythmia. In a preferred embodiment, these criteria involve measures of the degree of correlation of direction of movement between successive dipoles, and/or the magnitude of the dipole, and/or the dipole moment, and/or the degree of 'fit' of the dipole model to the measured data, and/or other dipole parameters. In another preferred embodiment, the location of the site of origin of the arrhythmia is then displayed on a graphical user interface.

In a preferred embodiment, the stimulating electrodes are used to stimulate the heart. In a particularly preferred embodiment the stimulating step involves pacing the heart at approximately the same rate as the rate of the arrhythmia. The locations of the one or more stimulating electrodes are identified by analyzing the electrical activity at a multiplicity of time epochs during the cardiac cycle. In a preferred embodiment, this involves computing the location of at least one equivalent moving dipole. A set of criteria may be applied to the analyses of electrical activity at a multiplicity of time epochs in order to determine the locations of the one or more stimulating electrodes. In a preferred embodiment, these criteria involve measures of the degree of correlation of direction of movement between successive dipoles, and/or the magnitude of the dipole, and/or the dipole moment, and/or the time elapsed since stimulation of the cardiac tissue, and/or the degree of 'fit' of the dipole model to the measured data, and/or other dipole parameters. In another preferred embodiment, the locations of the one or more stimulating electrodes are then displayed on a graphical user interface.

In a particularly preferred embodiment, the stimulating electrodes are advanced towards the site of origin of the arrhythmia. During this process, the stimulating, processing and advancing steps are performed iteratively. In another preferred embodiment, radio-frequency energy is then delivered to ablate the site of origin of the arrhythmia.

DESCRIPTION OF THE PREFERRED EMBODIMENTS

Previous patents (U.S. Pat. Nos. 6,308,093 and 6,370,412 discussed above) have described a method by which the electrical source of low-frequency electrical activity (such as a slow ventricular tachycardia) within the body can be localized and ablated. However, the ablation catheter tip cannot be accurately guided in the manner described in previous patents in the presence of a rapid arrhythmia (such as in cases of fast ventricular tachycardia, >240 beats per minute).

In previous methods, low-amplitude sub-threshold bipolar current pulses are delivered from an electrode at the tip of the catheter. The signals at the body surface result solely from the weak electrical fields set up in the body by the bipolar pulses. These surface signals are fitted with a moving dipole model to determine the relative location of the stimulating electrode within a given short time epoch. Thereafter, the processes of delivering electrical energy and determining the relative location of the stimulating electrode are repeated until the locations of the stimulating electrode tip and the site of origin of the arrhythmia are nearly identical. This method is only suitable for conditions of slow ventricular tachycardia. Slow ventricular tachycardia is characterized by a completion of the previous ventricular excitation and repolarization before the next ventricular excitation begins. It is evidenced by the presence of an isoelectric period between the T wave from the previous cardiac cycle and the QRS from the current cardiac cycle.

However, in cases of fast ventricular tachycardia, electrical activity from the previous cycle, now for the most part remote from the site of origin of the arrhythmia, is still present when the next wave of depolarization emerges from that site. The bioelectric source dipole is computed from the body surface potentials which in turn reflect a summation of all on-going electrical activity in the heart. At the start of the QRS complex during fast ventricular tachycardia the bioelectrical source dipole will be a summation of both the remote electrical activity associated with the previous cardiac cycle and the localized activity newly emerging from the site of origin of the arrhythmia. Consequently, the location of the bioelectric source dipole will no longer correspond to the location of the site of origin of the arrhythmia. Therefore, even if the catheter tip and site of origin of the arrhythmia are in reality superposed, the previously described method will identify their locations as being different. As a result, the method proposed in previous patents for matching an ablation catheter to the site of origin of the arrhythmia is suboptimal in the context of fast ventricular tachycardia. This problem is solved by our current innovation.

Figure 1:
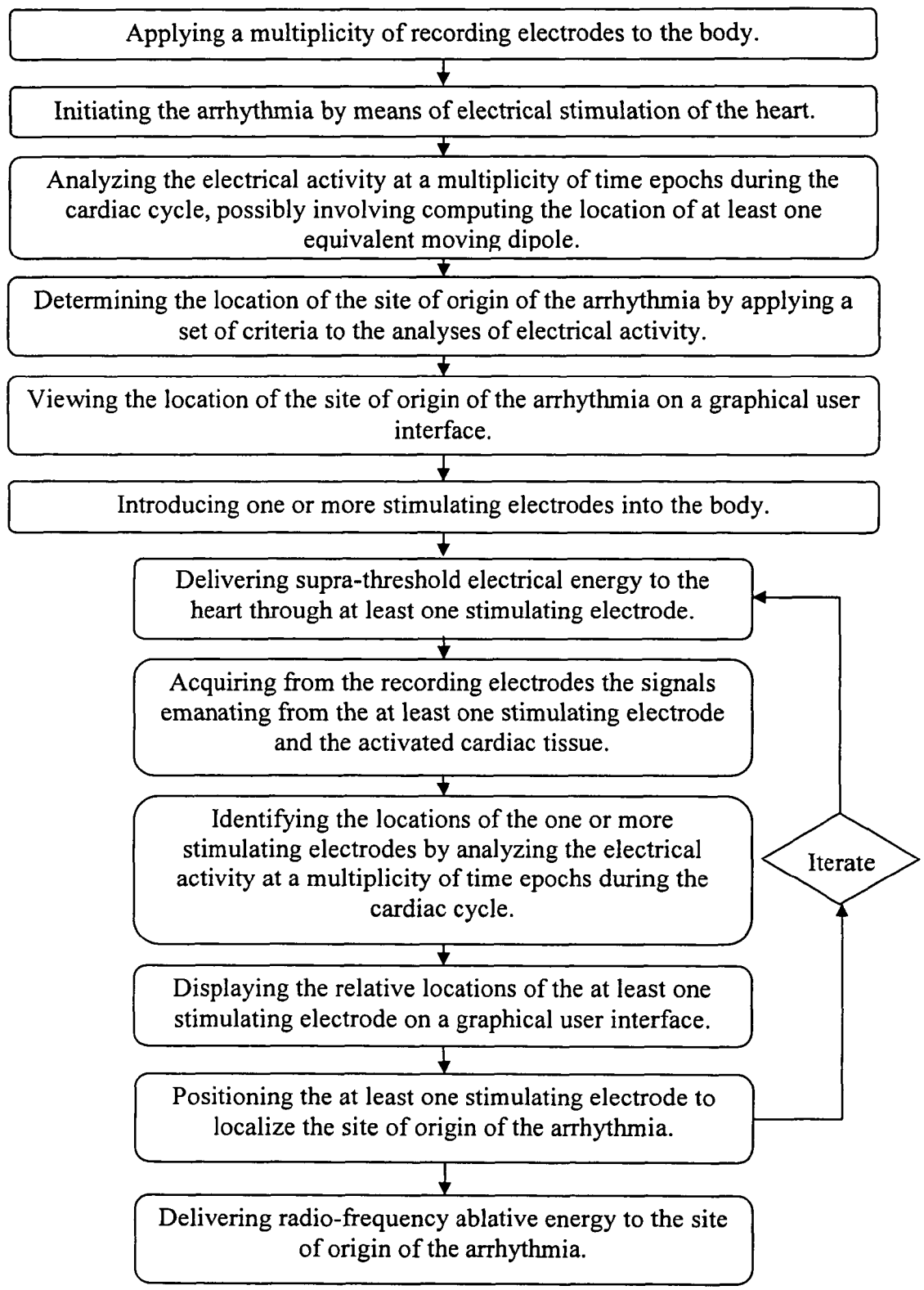
FIG. 1 is a flow chart of a preferred embodiment of the method for localizing a site of origin of the arrhythmia within the body.

FIG. 1 shows a flowchart of the method according to the present invention for localizing the site of origin of an arrhythmia within the body. The method involves applying a multiplicity of recording electrodes to the body. The signals from the recording electrodes are analyzed to identify the location of the site of origin of the arrhythmia. One or more stimulating electrodes are introduced into the body and are used to stimulate the heart with supra-threshold stimuli. The electrical activity recorded by the recording electrodes is processed to identify the locations of the one or more stimulating electrodes—this latter electrical activity reflects the signals emanating from both the stimulating electrode(s) and from the heart due to the stimuli from the stimulating electrode(s).

The stimulating electrodes may be used to pace the heart with supra-threshold stimuli at the same rate as the ventricular tachycardia, with at least two pacing stimuli applied. If the pacing and ventricular tachycardia rates are the same, and the stimulating electrode location(s) and site of origin of the arrhythmia are nearly superposed, the locations deduced from the analysis of the electrical signals from the recording electrodes of the site of origin of the arrhythmia and of the stimulating electrode(s) will also be approximately superposed. This is so because in both cases the locations are deduced from the electrical activity of the heart muscle which is stimulated in the same pattern whether originating from a bioelectrical source in the site of origin of the arrhythmia or from the stimulating electrode(s). Therefore, this method may be used to locate the site of origin of the arrhythmia by determining when the stimulating electrode(s) are approximately superposed on it.

In preferred embodiments of the invention, the arrhythmia is initiated by means of electrical stimulation of the heart and the resulting electrical activity is analyzed at a multiplicity of time epochs during the cardiac cycle. In a preferred embodiment, this analysis involves computing the location of an equivalent moving dipole for at least one time epoch. Computing the location of more than one equivalent moving dipole allows one to identify the site of origin of the arrhythmia by examining not only the initial electrical activity in the cardiac cycle but also the path the equivalent dipole follows after electrical activity leaves the site of origin of the arrhythmia. In a preferred embodiment, in order to determine the site of origin of the arrhythmia a set of criteria is applied to the analyses of electrical activity at the multiplicity of time epochs. These criteria may include measures of the dipole magnitude, dipole moment, the degree of 'fit' of the dipole model to the measured data, and/or the degree of correlation of direction of movement between successive dipoles. This latter criterion searches for the time epoch at which electrical activity begins moving away from the site of origin of the arrhythmia. At this time instant, we would expect movement between successive dipoles to become highly correlated.

Once the site of origin of the arrhythmia has been identified, in another preferred embodiment its location is displayed on a graphical user interface. If an equivalent moving dipole model was used in the analysis of electrical activity, features such as dipole size, strength, model fit and/or uncertainty in the dipole location may be simultaneously displayed on the interface.

As shown in FIG. 1, one or more catheters bearing stimulating electrodes at their tips are introduced into the body. In a preferred embodiment of the present invention, the heart is paced using supra-threshold pulses delivered by the at least one stimulating electrode while the heart is in sinus rhythm. The stimulating electrode(s) are close to or in contact with the cardiac tissue. Two signals are subsequently recorded at the torso surface: those due to the weak electric field created momentarily by the stimulating currents themselves, and those due to the regenerating electrical activity of the cardiac tissue activated by the supra-threshold stimulation. In a preferred embodiment, the locations of the one or more stimulating electrodes are identified by analyzing the electrical activity at a multiplicity of time epochs during the cardiac cycle. In another preferred embodiment, this involves computation of the location of at least one equivalent moving dipole. Computing the locations of more than one equivalent moving dipole allows one to identify not only the location of the stimulating electrode but also the path the equivalent dipole follows after the supra-threshold stimulus.

In a preferred embodiment, a set of criteria is applied to the analyses of signals at a multiplicity of time epochs to find the location(s) of the one or more stimulating electrodes. These criteria may include measures of the dipole magnitude, the dipole moment, the degree of 'fit' of the dipole model to the measured signals, the time elapsed since stimulation of the cardiac tissue, and/or the degree of correlation of direction of movement between successive dipoles. This latter criterion searches for the time epoch at which electrical activity begins moving through the cardiac tissue away from the site of application of the supra-threshold pulses. At this time instant, we would expect movement between successive dipoles to become highly correlated.

The stimulating electrodes may be used to pace the heart with supra-threshold stimuli at the same rate as the ventricular tachycardia, with at least two pacing stimuli applied at each location of the stimulating electrode(s). If the pacing and ventricular tachycardia rates are the same, and the stimulating electrode location and site of origin of the arrhythmia are nearly superposed, their two corresponding equivalent dipole locations will also be nearly superposed. This will be the case even though neither dipole may reflect the actual location of its electric source. By the same token, if their equivalent dipole locations are nearly identical we may be sure that the actual locations of the stimulating electrode(s) and site of origin of the arrhythmia are nearly identical. Therefore, this method may be used to locate the site of origin of the arrhythmia by determining when the stimulating electrode(s) are approximately superposed on it.

In one preferred embodiment, the locations of the one or more stimulating electrodes are displayed on a graphical user interface. In another preferred embodiment, the stimulating electrode(s) are advanced towards the site of origin of the arrhythmia. If the location of the site of origin of the arrhythmia is displayed on the graphical user interface along with the location(s) of the stimulating electrode(s), the interface will aid in the guidance of the stimulating electrode towards the site of origin of the arrhythmia.

In a particularly preferred embodiment, the processes of stimulating the cardiac tissue with supra-threshold energy, processing the signals emanating from the at least one stimulating electrode and activated cardiac tissue, and positioning the at least one stimulating electrode are performed iteratively. The process may be terminated when the site of origin of the arrhythmia and the stimulating electrode(s) are nearly superposed. Near-superposition may be indicated by near-alignment of the locations corresponding to the site of origin of the arrhythmia and the stimulating electrode(s). It may also be indicated by the similarity of the paths followed by the equivalent moving dipole over multiple time epochs. In a preferred embodiment of this invention, radio-frequency energy is then delivered to ablate the site of origin of the arrhythmia.

This method may also be applied in the localization of the site of origin of a slow arrhythmia, when there is no remote electrical activity present when the next depolarization begins. Therefore it may be used to guide ablative therapy in the context of an arrhythmia regardless of its rate.

Figure 2:
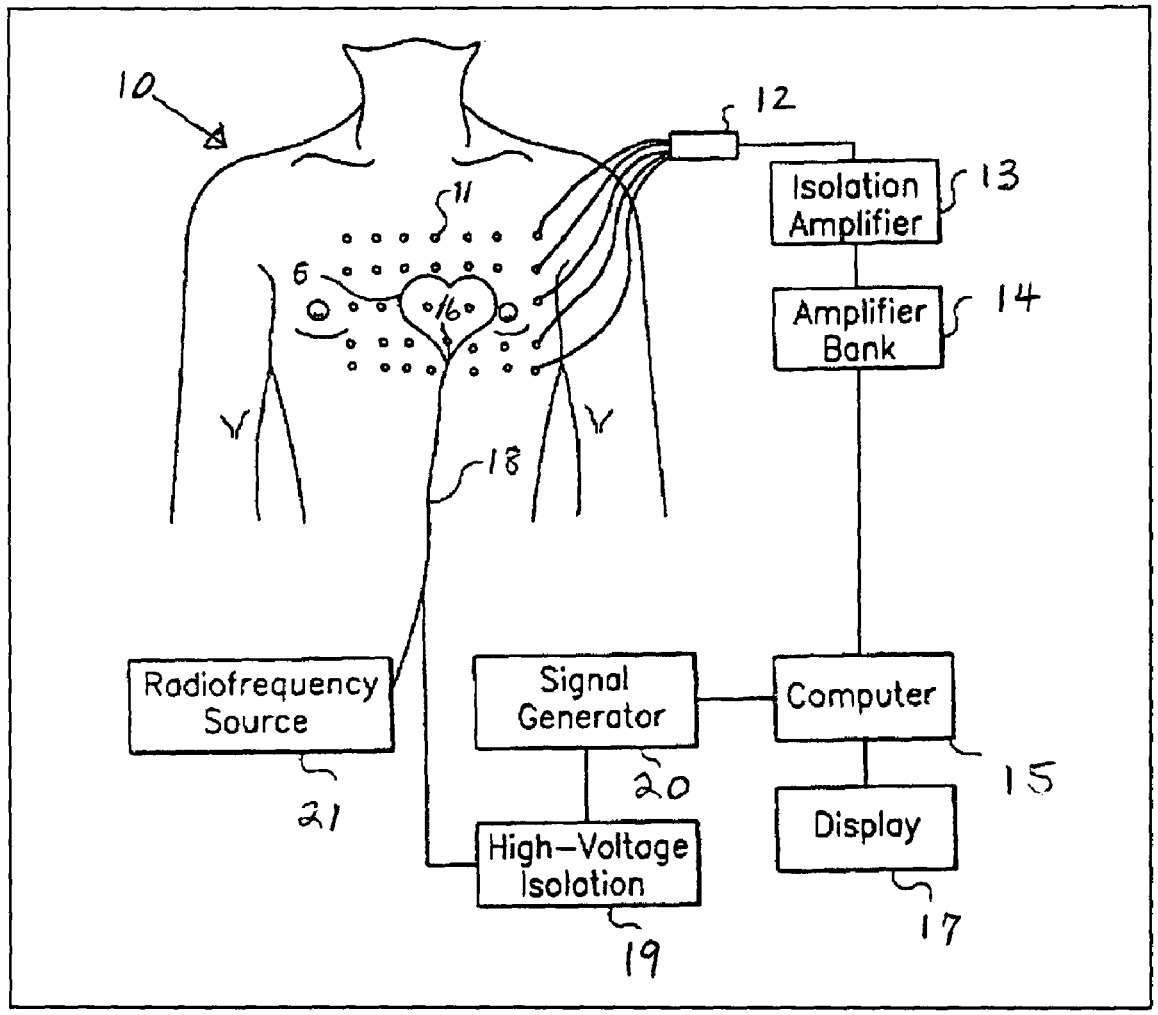
FIG. 2 is a schematic diagram of an apparatus for localizing a site of origin of an arrhythmia, guiding the delivery of ablative therapy, and delivering ablative therapy to the site of origin of the arrhythmia.

FIG. 2 shows a preferred embodiment of the system for localizing the site of origin of the arrhythmia, guiding the delivery of ablative energy, and delivering ablative energy to the vicinity of the site of origin of the arrhythmia. A multiplicity of recording electrodes 11 are placed on the body surface of a subject 10 such that the heart 6 may be viewed from the anterior, left lateral, right lateral, and posterior chest.

Each electrode 11 position is provided by the operator to the analysis software. Signals from the recording electrodes 11 are carried in a multi-lead cable 12 through an isolation amplifier 13 to an amplifier bank 14 with adjustable gain and frequency response. A computer 15 equipped with a multiplexor and an analog to digital conversion card digitizes and processes the signals emanating from the site of origin of the arrhythmia and the signals arising due to pacing by a stimulating electrode 16 placed within the heart 6. As described in detail above, in a preferred embodiment of the invention the processing step utilizes a single equivalent moving dipole (SEMD) model to localize both the site of origin of the arrhythmia and the stimulating electrode 16 at a series of time epochs. The computer 15 also creates an electronic representation of the signals acquired from each electrode 11, stores the signals, and displays the signals on a display 17. To inspect the signals the operator may display them off-line from storage at a rate slower than real time. The position, magnitude, and orientation of the SEMD attributed to cardiac electrical activity at each time epoch are displayed in a three-dimensional view of the heart 6. The uncertainty in the position of the SEMD and the goodness-of-fit value of the estimation of the SEMD parameters may also be displayed for each time epoch.

An ablation catheter 18 with its at least one stimulating electrode 16 is placed in the heart 6 of the subject. The catheter 18 is connected through a high-voltage isolation stage 19 that serves as an automatic switch (the switch automatically turns off the signal generator circuit after sensing the radio frequency source) to a signal generator 20, which is controlled by the computer 15 and can generate a supra-threshold signal (of sufficient magnitude to pace the heart). The position, magnitude, and orientation of the dipole attributed to the tip of the catheter are displayed for each time epoch. The uncertainty in the position of the dipole attributed to the tip of the catheter and the goodness-of-fit value of the estimation of the dipole parameters attributed to the tip of the catheter 18 are also displayed for each time epoch. A radio frequency source 21 controlled by the operator is also attached to the ablation catheter 18. After localization of the source of abnormal electrical activity (i.e., the site of origin of the arrhythmia) and positioning of the tip of the catheter 18 at the source of abnormal electrical activity as described above, the catheter 18 is used to deliver ablative radio frequency energy to the vicinity of the site of origin of the arrhythmia.

The present invention thus provides methods and apparatus for localizing the site of origin of an arrhythmia. The invention further provides methods and apparatus for delivering ablative electrical energy in the vicinity of the site of origin of the arrhythmia. The present invention is particularly applicable in the context of fast ventricular arrhythmias, although it may be used in any context in which an ablation catheter must be guided to a focused source of electrical activity.

Cardiac arrhythmias are frequently treated by delivering electrical energy to the site of origin of the arrhythmia in an effort to ablate the site. To effectively perform this procedure, accurate localization of both the site of origin of the arrhythmia and the energy delivery device (e.g., the tip of a catheter) are necessary. As used herein, the term "localization" refers to determining either an absolute or a relative location. The present invention thus provides techniques for accurately performing such localization. The minimally invasive and fast aspects of certain embodiments of the invention, as disclosed herein, are particularly important.

REFERENCES

The contents of all of the following references are incorporated herein by reference in their entirety.

A. A. Armoundas, "A Novel Technique for Guiding Ablative Therapy of Cardiac Arrhythmias," in *Nuclear Engineering*. Cambridge: MIT, 1999, pp. 179.

A. A. Armoundas, A. B. Feldman, D. A. Sherman, and R. J. Cohen, "Applicability of the single equivalent point dipole model to represent a spatially distributed bio-electrical source," *Med Biol Eng Comput*, vol. 39, pp. 562-70, 2001.

A. A. Armoundas, A B Feldman, R Mukkamala, and R J Cohen, "A Single Equivalent Moving Dipole Model: An Efficient Approach for Localizing Sites of Origin of Ventricular Electrical Activation," *Annals of Biomedical Engineering*, vol. 31, pp. 564-576, 2003.

Barley, M., Design and Implementation of a Device User Interface for the Guided Ablative Therapy of Cardiac Arrhythmias, in EECS. 2003, MIT: Cambridge.

De Bakker J C T, van Capelle F J L, Janse M J, van Hemel N M, Hauer R N W, Defauw J, Vermeulen F, de Wekker P. Macroreentry in the infarcted human heart: mechanism of ventricular tachycardias with a focal activation pattern. J Am Coll Cardiol., 1991;18: 1005-1014.

Einthoven W. The different forms of the human electrocardiogram and their signification, Lancet, 1912;853-861.

Gabor D and Nelson C V. Determination of the resultant dipole of the heart from measurements on the body surface. J Appl Physics, 1954;25:413-416.

Gomick C C, Stuart S W, Pederson B, Hauck J, Budd J, Schweitzer J. Validation of a new noncontact catheter system for electroanatomic mapping of left ventricular endocardium. Circulation, 1999;99,829-835.

Gepstein L, Hayam G, Ben-Haim S A. Activation-repolarization coupling in the normal swine endocardium. Circulation, 1997;96:4036-4043.

Gulrajani R M, Pham-Huy H, Nadem R A, et al. Application of the single moving dipole inverse solutions to the study of the WPW syndrome in man. J Electrocardiol, 1984;17: 271-288.

Kaltenbrunner W, Cardinal R, Dubuc M, Shenasa M, Nadeau R, Tremblay G, Vermeulen M, Savard P, Page P L. Epicardial and endocardial mapping of ventricular tachycardia in patients with myocardial infarction: is the origin of the tachycardia always subendocardially localized. Circulation, 1991;84,1058-1071.

Kim Y H, Sosa-Suarez G, Trouton T G, O'Nunain S S, Osswald S, McGovern B A, Ruskin J N, Garan H. Treatment of ventricular tachycardia by transcatheter radiofrequency ablation in patients with ischemic heart disease. Circulation, 1994;89:1094-1102.

Kottkamp H, Hindricks G, Breithardt G, Borggrefe M. Three-Dimensional Electromagnetic Catheter Technology: Electroanatomical Mapping of the Right Atrium and Ablation of Ectopic Atrial Tachycardia. J Cardiovasc Electrophysiol, 1997;8:1332-1337.

Langberg J J, Calkins H, Kim Y N, et al. Recurrence of conduction in accessory atrioventricular connections after initially successful radiofrequency catheter ablation. J Am Coll Cardiol, 1992;19:1588-1592.

Langberg J J, Harvey M, Caikis H, el-Atassi R, Kalbfleish S J, Morady F. Titration of power output during radiofrequency catheter ablation of atrioventricular nodal reentrant tachycardia. Pacing Clin Electrophysiol, 1993;16;465-470.

Lee M A, Morady F, Kadish A, et al. Catheter modification of the atrioventruclar junction with radiofrequency energy for control of atrioventricular nodal reentry tachycardia. Circulation, 1991;83:827-835.

Mirvis D M, Hollrook M A. Body surface distributions of repolarization potentials after acute myocardial infarction. III. Dipole ranging in normal subjects and in patients with acute myocaridial infarction. J Electrocardiol, 1981;14: 387-98.

Mitrani R D, Biblo L A, Carlson M D, Gatzoylis K A, Hentom R W, Waldo A L. Multiple monomorphic ventricular tachycardia configurations predict failure of antiarrhythmic drug therapy guided by electrophysiologic study. J Am Coll Cardiol, 1993;22:1117-1122.

Miller J M, Kienzle M, Harken A H, Josephson M E. Subendocardial resection for ventricular tachycardia: predictors of surgical success. Circulation, 1984;70:624-631.

Morady F, Harvey M, Kalbfleisch S J, El-Atassi R, Calkins H, Langberg J J. Radiofrequency catheter ablation of ventricular tachycardia in patients with coronary artery disease. Circulation, 1993;87:363-372.

Nademanee K, Kosar E M. A Nonfluoroscopic Catheter-Based Mapping Technique to Ablate Focal Ventricular Tachycardia. PACE, 1998;21:1442-1447.

Nakagawa H. Jackman W M. Use of a Three-Dimensional, Nonfluoroscopic Mapping System for catheter ablation of Typical Atrial Flutter. PACE, 1998;21:1279-1286.

Natale A, Breeding L, Tomassoni G, Rajkovich K, Richey M, Beheiry S, Martinez K, Cromwell L, Wides B, Leonelli F. Ablation of Right and Left Ectopic Atrial Tachycardias Using a Three-Dimensional Nonfluoroscopic Mapping System. Am J Cardiol, 1998;82:989-992.

Nath S, Whayne J G, Kaul S, Goodman N C, Jayaweera A R, Haines D E. Effects of radiofrequency catheter ablation on regional myocardial blood flow: possible mechanism for late electrophysiological outcome. Circulation, 1994;89: 2667-2672.

Paul T, Moak J P, Morris C, et al. Epicardial mapping: How to measure local activation? PACE, 1990;13:285.

Shah D C, Jais P, Haissaguerre M, Chouairi S, Takahashi A, Hocini M, Garrigue S, Clementy J. Three dimensional Mapping of the Common Atrial Flutter Circuit in the Right Atrium. Circulation, 1997;96:3904-3912.

Schilling R J, Davies D W, Peters N S. Characteristics of Sinus Rhythm Electrograms at Sites of Ablation of Ventricular Tachycardia Relative to All Other Sites: A Noncontact Mapping Study of the Entire Left Ventricle. J Cardiovasc Electrophysiol, 1998;9:921-933.

Smith J M, Clancy E A, Valeri C R, Ruskin J N, Cohen R J. Electrical alterants and cardiac electrical instability. Circulation, 1988;77:110-121.

Shpun S, Gepstein L, Hayam G, Ben-Haim S A. Guidance of radiofrequency endocardial ablation with real-time three-dimensional magnetic navigation system. Circulation, 1997;96:2016-2021.

Stevenson W G, Friedman P L, Ganz L I. Radiofrequency Catheter Ablation of Ventricular Tachycardia Late After Myocardial Infarction. J Cardiovasc Electrophysiol, 1997; 8:1309-1319.

Stevenson W G, Delacretaz E, Friedman P L, Ellison K E. Identification and Ablation of Macroreentrant Ventricular Tachycardia with the CARTO Electroanatomical Mapping System. PACE, 1998;21:1448-1456.

Stevenson W G, Friedman P L, Kocovic D, Sager P T, Saxon L A, Pavri B. Radiofrequency catheter ablation of ventricular tachycardia after myocardial infarction. Circulation, 1998;98:308-314.

Strickberger S A, Man K C, Daoud E G, et al. A prospective evaluation of catheter ablation of ventricular tachycardia as adjuvant therapy in patients with coronary artery disease and an implantable cardioverter-defibrillator. Circulation, 1997;96:1525-1531.

Tsunakawa H, Nishiyama G, Kanesaka S, Harumi K. Application of dipole analysis for the diagnosis of myocardial infarction in the presence of left bundle branch block. J Am Coll Cardiol, 1987;10:1015-21.

Waspel L E, Brodman R, Kim S G, Matos J A, Johnston D R, Scavin G M, Fisher J D. Activation mapping in patients with coronary artery disease with multiple ventricular tachycardia configurations: occurrence and therapeutic implications of widely separate apparent sites of origin. J Am Coll Cardiol, 1985;5:1075-1086.

Wilber D J, Davis M J, Rosenbaum D S, Ruskin J N, Garan H. Incidence and determinants of multiple morphologically distinct sustained ventricular tachycardias. J Am Coll Cardiol, 1987;10:589-591.

It is recognized that modifications and variations of the present invention will occur to those skilled in the art, and it is intended that all such modifications and variations be included within the scope of the appended claims.

What is claimed is:

1. Method for locating a site of origin of an arrhythmia, comprising:
    applying a multiplicity of recording electrodes to a body;
    analyzing electrical activity from the recording electrodes to identify a location of the site of origin of the arrhythmia;
    introducing one or more stimulating electrodes into the body;
    stimulating a heart with supra-threshold stimuli through the one or more stimulating electrodes; and
    processing the electrical activity from the recording electrodes to identify locations of the one or more stimulating electrodes in relation to the location of the site of origin of the arrhythmia.

2. The method of claim 1 further comprising initiation of the arrhythmia by electrical stimulation of the heart.

3. The method of claim 1 wherein the analyzing step is used to identify the location of the site of origin of the arrhythmia by analyzing the electrical activity at a multiplicity of time epochs during a cardiac cycle.

4. The method of claim 1 wherein the analyzing step includes computing a location of at least one equivalent moving dipole.

5. The method of claim 3 wherein the analyzing step includes application of a set of criteria to the analyses of electrical activity at the multiplicity of time epochs in order to determine the site of origin of the arrhythmia.

6. The method of claim 5 wherein the criteria include measures of a degree of correlation of direction of movement between successive dipoles, and/or a magnitude of a dipole, and/or a dipole moment, and/or a degree of 'fit' of a dipole model to measured data, and/or other dipole parameters.

7. The method of claim 1 wherein the location of the site of origin of the arrhythmia is displayed on a graphical user interface.

8. The method of claim 1 wherein the processing step is used to identify the locations of the one or more stimulating electrodes by analyzing the electrical activity at a multiplicity of time epochs during a cardiac cycle.

9. The method of claim 1 wherein the stimulating step includes pacing the heart at approximately the same rate as the rate of the arrhythmia.

10. The method of claim 1 wherein the processing step includes computing a location of at least one equivalent moving dipole.

11. The method of claim 8 wherein the processing step includes application of a set of criteria to the analyses of electrical activity at the multiplicity of time epochs in order to determine the locations of the one or more stimulating electrodes.

12. The method of claim 11 wherein the criteria involve measures of a degree of correlation of direction of movement between successive dipoles, and/or a magnitude of a dipole, and/or a dipole moment, and/or a time elapsed since stimulation of the cardiac tissue, and/or a degree of 'fit' of a dipole model to the measured data, and/or other dipole parameters.

13. The method of claim 1 wherein the locations of the one or more stimulating electrodes are displayed on a graphical user interface.

14. The method of claim 1 further comprising advancing of the one or more stimulating electrodes towards the site of origin of the arrhythmia.

15. The method of claim 14 wherein the stimulating, processing and advancing steps are performed iteratively.

16. The method of claim 1 further comprising delivering radio-frequency energy to ablate the site of origin of the arrhythmia.

* * * * *